United States Patent [19]
Held et al.

[11] Patent Number: 5,830,419
[45] Date of Patent: Nov. 3, 1998

[54] APPARATUS AND METHOD FOR PROCESSING MEDICAL WASTE

[75] Inventors: Jeffery S. Held, Chicago; James W. Sharp, Arlington Heights, both of Ill.

[73] Assignee: Stericycle, Inc., Deerfield, Ill.

[21] Appl. No.: 486,394

[22] Filed: Jun. 7, 1995

Related U.S. Application Data

[63] Continuation of Ser. No. 177,803, Jan. 6, 1994, Pat. No. 5,508,004, which is a continuation of Ser. No. 826,022, Jan. 27, 1992, abandoned, which is a division of Ser. No. 586,442, Sep. 21, 1990, Pat. No. 5,106,594, which is a continuation-in-part of Ser. No. 502,293, Mar. 30, 1990, abandoned, and a continuation-in-part of Ser. No. 530,438, Jun. 1, 1990, Pat. No. 5,035,858, which is a continuation of Ser. No. 421,332, Oct. 3, 1989, abandoned.

[51] Int. Cl.$^6$ ............................... A61L 2/12; H05H 6/64
[52] U.S. Cl. ........................ 422/307; 422/21; 241/606; 219/679
[58] Field of Search .................. 422/21, 22, 32, 422/307, 308, 900; 241/606; 219/679

[56] References Cited

U.S. PATENT DOCUMENTS

| | | |
|---|---|---|
| 2,114,345 | 4/1938 | Hayford . |
| 2,486,684 | 11/1949 | Schlesman et al. . |
| 2,542,028 | 2/1951 | Hodge . |
| 2,564,579 | 8/1951 | Parmenter et al. . |
| 2,731,208 | 1/1956 | Dodd . |
| 2,897,365 | 7/1959 | Dewey et al. . |
| 2,958,570 | 11/1960 | Fessler . |
| 3,095,359 | 6/1963 | Heller . |
| 3,215,539 | 11/1965 | Landy . |
| 3,261,140 | 7/1966 | Long et al. . |
| 3,329,796 | 7/1967 | Manwaring . |
| 3,387,378 | 6/1968 | Newsom . |
| 3,490,580 | 1/1970 | Brumfield et al. . |
| 3,494,723 | 2/1970 | Gray . |
| 3,494,724 | 2/1970 | Gray . |
| 3,547,577 | 12/1970 | Lovercheck . |
| 3,551,090 | 12/1970 | Brumfield et al. . |
| 3,589,276 | 6/1971 | Swallert . |
| 3,602,712 | 8/1971 | Mann . |
| 3,617,178 | 11/1971 | Clouston . |
| 3,704,089 | 11/1972 | Stehlik . |

(List continued on next page.)

FOREIGN PATENT DOCUMENTS

| | | |
|---|---|---|
| 0098595 | 1/1984 | European Pat. Off. . |
| 2078203 | 11/1971 | France . |
| 271454 | 9/1989 | German Dem. Rep. ................. 422/21 |
| 3710156 | 10/1988 | Germany . |
| 1123705 | 11/1984 | U.S.S.R. . |
| 532502 | 1/1941 | United Kingdom . |
| 942374 | 11/1963 | United Kingdom . |
| 1406789 | 9/1975 | United Kingdom . |
| 2 130 060 | 5/1984 | United Kingdom . |
| 2 166 633 | 5/1986 | United Kingdom . |

OTHER PUBLICATIONS

Chipley. "Effects of Microwave Irradiation on Microorganisms." *Advances in Applied Microbiology.* vol. 26 (1980), pp. 129–145.

Bill Paul. "Combustion Says Firm Sterilizes Medical Waste With Microwaves." *The Wall Street Journal*, p. B3 (Apr. 10, 1989).

"Science Watch: Microwave Sterilizer is Developed." *New York Times.* (Jun. 20, 1989).

"Mechanism of Microwave Sterilization in the Dry State." Unkonwn source and publication date.

"Medical Waste Treatment by Microwave Technology", Norcal Solid Waste Systems, date unkown.

(List continued on next page.)

*Primary Examiner*—Robert J. Warden
*Assistant Examiner*—E. Leigh McKane
*Attorney, Agent, or Firm*—Brinks Hofer Gilson & Lione

[57] ABSTRACT

An apparatus and method for processing medical waste are disclosed. Medical waste is disintegrated or shredded, disinfected with radio-frequency electromagnetic radiation and then transformed into useful material such as reclaimed plastic and refuse-derived fuel.

4 Claims, 4 Drawing Sheets

U.S. PATENT DOCUMENTS

| | | |
|---|---|---|
| 3,736,111 | 5/1973 | Gardner et al. . |
| 3,736,120 | 5/1973 | Tempe . |
| 3,742,180 | 6/1973 | Bradley . |
| 3,753,651 | 8/1973 | Boucher . |
| 3,783,217 | 1/1974 | Brown . |
| 3,861,117 | 1/1975 | DeFilippi ................................. 100/97 |
| 3,885,119 | 5/1975 | Sargeant . |
| 3,885,915 | 5/1975 | Utsumi et al. . |
| 3,926,379 | 12/1975 | Dryden et al. . |
| 3,926,556 | 12/1975 | Boucher . |
| 3,929,295 | 12/1975 | Montalbano . |
| 3,940,325 | 2/1976 | Hirao . |
| 3,948,601 | 4/1976 | Fraser et al. . |
| 3,958,765 | 5/1976 | Musselman . |
| 3,958,936 | 5/1976 | Knight, Jr. . |
| 4,072,273 | 2/1978 | Reiniger ................................. 241/24 |
| 4,140,537 | 2/1979 | Luck I . |
| 4,148,614 | 4/1979 | Kirkbride . |
| 4,151,419 | 4/1979 | Morris et al. . |
| 4,175,885 | 11/1979 | Jeppson . |
| 4,205,794 | 6/1980 | Horton et al. . |
| 4,207,286 | 6/1980 | Gut Boucher . |
| 4,250,139 | 2/1981 | Luck II . |
| 4,252,459 | 2/1981 | Jeppson . |
| 4,252,487 | 2/1981 | Jeppson . |
| 4,264,352 | 4/1981 | Houser . |
| 4,276,093 | 6/1981 | Pickermann . |
| 4,295,908 | 10/1981 | Schaefer et al. . |
| 4,341,353 | 7/1982 | Hamilton et al. . |
| 4,347,016 | 8/1982 | Sindelar et al. . |
| 4,374,491 | 2/1983 | Stortroen et al. . |
| 4,376,033 | 3/1983 | Calderon . |
| 4,376,034 | 3/1983 | Wall . |
| 4,398,076 | 8/1983 | Hanson . |
| 4,400,357 | 8/1983 | Hohmann . |
| 4,457,221 | 7/1984 | Geren . |
| 4,510,363 | 4/1985 | Reynolds, Jr. . |
| 4,524,079 | 6/1985 | Hofmann . |
| 4,552,720 | 11/1985 | Baker Sr. et al. . |
| 4,563,259 | 1/1986 | Rayner . |
| 4,569,736 | 2/1986 | Kosegaki . |
| 4,599,216 | 7/1986 | Rohrer I . |
| 4,619,550 | 10/1986 | Jeppson . |
| 4,620,908 | 11/1986 | Van Duzer . |
| 4,652,763 | 3/1987 | Nablo . |
| 4,670,634 | 6/1987 | Bridges et al. . |
| 4,671,935 | 6/1987 | Rohrer II . |
| 4,706,560 | 11/1987 | Capodicasa . |
| 4,710,318 | 12/1987 | Horiuchi et al. . |
| 4,746,946 | 5/1988 | Wear et al. . |
| 4,746,968 | 5/1988 | Wear et al. . |
| 4,775,770 | 10/1988 | Fritz . |
| 4,801,427 | 1/1989 | Jacob . |
| 4,808,782 | 2/1989 | Nakagawa et al. . |
| 4,808,783 | 2/1989 | Stenstrom . |
| 4,818,488 | 4/1989 | Jacob . |
| 4,830,188 | 5/1989 | Hannigan et al. . |
| 4,874,134 | 10/1989 | Wiens . |
| 4,884,756 | 12/1989 | Pearson . |
| 4,896,010 | 1/1990 | O'Connor et al. . |
| 4,917,586 | 4/1990 | Jacob . |
| 4,931,261 | 6/1990 | Jacob . |
| 4,943,417 | 7/1990 | Jacob . |
| 4,974,781 | 12/1990 | Placzek . |
| 4,978,501 | 12/1990 | Diprose et al. . |
| 4,984,748 | 1/1991 | Kimura . |
| 4,988,044 | 1/1991 | Weitzmann et al. . |
| 5,019,344 | 5/1991 | Kutner et al. . |
| 5,035,858 | 7/1991 | Held et al. . |
| 5,048,766 | 9/1991 | Gaylor et al. . |
| 5,077,007 | 12/1991 | Pearson . |
| 5,106,594 | 4/1992 | Held et al. . |
| 5,226,065 | 7/1993 | Held et al. . |

OTHER PUBLICATIONS

Christensen et al. "The Multi–Purpose Irradiation Plant and the Quality Control of Radiation Sterilization Of Medical Equipment." *Proceedings of the Fourth International Conference on the Peaceful Uses of Atomic Energy* (held in 1971), vol. 14 (1972), pp. 345–354.

"Gamma Processing Equipment", AECL Industrial Irradiation Division, (Jan. 1987).

Serota. "Heating With Radio Waves." *Automation* (Sep. 1973).

Center for Materials Fabrication. "Dielectric Heating: RF and Microwave." *TechCommentary*, vol. 4, No. 1 (1987), pp. 1–4.

Reynolds et al. "Thermoradiation Inactivation of Naturally Occuring Bacterial Spores in Soil." *Applied Microbiology*, vol. 28, No. 3 (Sep. 1974), pp. 406–410.

Brannen. "A Kinetic Model for the Biological Effects of Ionizing Radiation." Report No. SAND74–0269, Sandia Laboratories, Albuquerque, New Mexico, printed Oct. 1974, pp. 1–38.

1976 Progress Report—"Beneficial Uses Program–Period Ending December 31, 1976." Report No. SAND 77–0426, Sandia Laboratories, Albuquerque, New Mexico, printed Mar. 1977, pp. 3–44.

"Dielectric Heating", PSC, Inc., (date unknown).

Sivinski. "General Description of the Sludge Irradiation Process." *National Symposium on the Use of Cesium–137 to Process Sludge for Further Reduction of Pathogens* (held in Denver, Colorado, Sep. 3–4, 1980). Published Dec. 1980, pp. 57–68.

Tonetti. "Disease Control Requirements for Various Sludge Uses." *National Symposium on the Use of Cesium–137 to Process Sludge for Further Reduction of Pathogens* (held in Denver, Colorado, Sep. 3–4, 1980). Published Dec. 1980, pp. 43–56.

"Electromagnetic Radiation and Ionizing Energy." (unknown source and publication date), pp. 6–8, 32–33, and 35–50.

Ward. "Molecular Mechanisms of Radiation–Induced Damage to Nucleic Acids." (unknown source and publication date), pp. 181–239.

Markitanova et al. "Study of Reagentless Sterilization of Wastewater." *Journal of Applied Chemistry of the USSR*, vol. 59, No. 11/part 2 (Nov. 1986), pp. 2365–2368.

Hall, S. K. "Infectious Waste Managements: A Multi–Faceted Problem." *Pollution Engineering* (Aug. 1989), pp. 74–78.

*United States Pharmacopoeia XX:* Section 1211, "Sterilization," pp. 1037–1040.

Morganstern. "The Future of Radiation Sterilization." *Second Johnson & Johnson Conference on Sterilization of Medical Products by Ionizing Radiation* (held in Vienna, Austria, Apr. 25–28, 1977), pp. 1–26. Published Jun. 15, 1977.

*Sterling's Elutriator.* Sterling Systems, A Division of The Sterling Blower Company, Forest, Virginia. Published Jun. 1989.

*Innovative Technology From The Sterling Blower Company.* Sterling Systems, A Division of The Sterling Blower Company, Forest, Virginia. Published Jun. 1989.

Boucher, "Advances In Sterilization Techniques–state of the Art and Recent Breakthroughs", Amer. Jour. of Hospital Pharmacy, vol. 29, Aug. 1972, pp. 661–672.

"Induction and Dielectric Heating," by Cable, J. Wesley, published by Reinhold Publishing Corp., New York, New York, (1954), pp. 501–512.

APPARATUS AND METHOD FOR PROCESSING MEDICAL WASTE

This application is a continuation of application Ser. No. 08/177,803, filed Jan. 6, 1994, (now U.S. Pat. No. 5,508,004, which was a continuation of application Ser. No. 07/826,022, filed Jan. 27, 1992, (now abandoned), which was a divisional of application Ser. No. 07/586,442, filed Sep. 21, 1990, now U.S. Pat. No. 5,106,594, which is a continuation-in-part of application Ser. No. 07/502,293, filed Mar. 30, 1990, (now abandoned) and a continuation-in-part of application Ser. No. 07/530,438, filed Jun. 1, 1990, now U.S. Pat. No. 5,035,858, which is a continuation of application Ser. No. 07/421,332, filed Oct. 13, 1989, (now abandoned).

BACKGROUND OF THE INVENTION

The present invention relates generally to a method of processing medical waste and more particularly to a method of disinfecting and converting medical waste to a form in which it can be beneficially used, such as purified, granulated plastic. The processing method includes breaking up the waste into fragments, exposing the waste fragments to radio-frequency radiation, and converting the disinfected fragments into useful components. The term medical waste encompasses not only medical waste but also veterinary waste. The categories and composition of medical waste are discussed first, followed by problems with current waste handling methods.

Medical waste disposal is of urgent concern because the waste may cause infection. Such infectious waste is a by-product of medical and veterinary care. For example, regulated medical waste consists of the following categories:

1. Cultures and stocks of infectious agents and associated biologicals;
2. Pathological wastes;
3. Human blood and blood products;
4. Contaminated "sharps", including needles, syringes, blades, scalpels, and broken glass;
5. Animal waste;
6. Isolation waste, including gloves and other disposable products used in the care of patients with serious infections; and
7. Unused "sharps".

Hospitals typically segregate these categories of waste into three general groups: a) general medical waste, including waste listed above in categories 1, 2, and 3; b) veterinary waste, or category 5; and c) waste that is predominantly plastic, including categories 4 and 6. Contaminated sharps and isolation waste are categories of special concern, as this waste may have been exposed to highly dangerous infections such as AIDS or hepatitis. Sharps in particular have caused deep public concern when observed on beaches and other public areas.

Hospitals and other generators of medical and veterinary waste employ three main methods of waste handling: 1) on-site incineration of the waste, 2) on-site steam autoclaving of the waste and later shipment to a landfill, and 3) no on-site processing before turning the waste over to a waste hauler.

Predominantly located in urban areas, many hospital incinerators emit pollutants at a relatively high rate. In the emissions of hospital incinerators, the Environmental Protection Agency (EPA) has identified harmful substances, including metals such as arsenic, cadmium, and lead; dioxins and furans; organic compounds like ethylene, acid gases, and carbon monoxide; and soot, viruses, and pathogens. Emissions from these incinerators may be a bigger public health threat than improper dumping. (Stephen K. Hall, "Infectious Waste Management: A multi-faceted Problem," Pollution Engineering, 74–78 (August 1989)).

Although steam autoclaving may be used to disinfect waste before further processing, it is expensive and time-consuming. Heat rapidly inactivates viruses; but bacteria survive somewhat longer than viruses. Bacterial spores can be highly resistant to heat sterilization. To assure effective disinfection, temperature monitoring devices such as thermocouples and biological indicators such as heat-resistant *Bacillus stearothermophilus* spores may be used.

U.S. Pat. No. 2,731,208 to Dodd teaches a steam-sterilizing apparatus for disposing of contaminated waste which shreds waste ("including paper containers such as used sputum cups," Col. 1, lines 28–29), blows steam into a container full of shredded waste and pours the disinfected waste into a sewage system. This process has several drawbacks, including processing of only limited types of items and depositing the processed waste into a sewer (Col. 4, line 49).

Soviet Union Inventor's Certificate No. 1,123,703 also discloses a method of sterilizing medical instruments for reuse by UHF treatment. For injection needles it discloses a final temperature of 160° to 470° C. and for acupuncture needles it discloses a final temperature of 160° to 270° C.

U.S. Pat. No. 3,958,936 to Knight teaches compaction of hospital waste for more efficient landfill disposal. Specifically, this reference teaches the application of heat in the range of about 400° to 600° F. to hospital and other waste to melt the plastic and turn it into a hard, compact block for safer disposal in landfills. The waste is disinfected and needles become imbedded in the plastic. This method has the disadvantages of requiring high energy expenditure to attain high temperatures and landfill disposal.

U.S. Pat. No. 3,547,577 to Lovercheck discloses a portable device for treating garbage such as trash, domestic refuse and the like (Col. 1, lines 13–19). The machine shreds garbage, compresses the shredded garbage into briquettes, and sterilizes the briquettes with ethylene oxide gas (Col. 1, lines 15–19). After shredding, the garbage may be separated into magnetic and non-magnetic portions (Col. 2, lines 13–23). After the garbage is so separated, only the non-magnetic portion is compressed into briquets and sterilized (Col. 2, lines 23–25). The sterilization step employs ethylene oxide gas which requires temperature control (Col. 2, lines 30–57). Thus, the briquettes are maintained at a temperature of about 54° C. (Col. 2, line 51). A drawback of this system is that both heat and poisonous gas are required to disinfect the garbage. Another drawback is that when the waste stream is divided into metal, water and briquets, only part of the waste stream (the briquets without metal or water) is disinfected. An additional disadvantage is that the volume of the waste stream is limited in that only one briquet is formed at a time. Another drawback is that the material is disposed in a landfill or by incineration. Although use as a fertilizer is suggested (Col. 1, line 47), there is no teaching that the briquets are really suited for that use or how the briquets could be further processed for that use.

Various energy sources are being considered as potential sterilants. Microwaves are increasingly being investigated for rapid sterilization of individual medical devices and shredded medical waste. Recently, an experiment showed that metallic instruments could be disinfected in only 30 seconds in a microwave chamber. (*N.Y. Times,* "Science Watch: Microwave Sterilizer is Developed," Jun. 20, 1989). A problem is that this particular method can handle only a few instruments at a time.

According to one publication, a medical waste disposal system utilizing microwaves has apparently been developed. This system first shreds medical waste, sprays it with water and spreads the small pieces in a thin layer on a conveyor belt. Then, the conveyor carries the mixture through a microwave chamber which heats the mixture to about 96° C. The waste can be routed to a steaming station where steam is applied to inactivate surviving microorganisms. After the disinfection step, the waste is packaged for shipment to landfills or incinerators. (*The Wall Street Journal,* p. B3, Apr. 10, 1989).

Further, microwaves are limited in their penetration. If applied to large-scale, boxed medical waste, the microwaves alone do not heat very effectively. In contrast, radio-frequency (RF) waves are relatively low-frequency waves which penetrate more effectively. RF waves have been used directly and indirectly for sterilization.

U.S. Pat. No. 3,948,601 to Fraser et al. teaches the indirect use of RF waves in disinfecting a wide variety of medical and hospital equipment as well as human waste. This reference teaches the use of RF waves to heat certain gases (particularly argon) to ionize into gas plasma at approximately 100° to 500° C. This references teaches that "cool" plasma (Col. 1, line 12) effectively sterilizes an article at a temperature of only 25° to 50° C. and very low pressure. However, sterilization by plasma gas does not suggest the direct use of RF waves in sterilization.

Whether or not the hospital first autoclaves its medical waste, including broken needles and glass, the waste is then turned over to a waste handler for transport to a landfill or other depository.

There are several problems with that disposal method. First, landfills, particularly in many urban areas, are becoming filled. In addition, older landfills may leak toxic chemicals into the surrounding earth and contaminate the water supply. Thus, burying wastes is becoming more of a concern. Also, unauthorized dumping may occur. What was needed before the present invention was a method to disinfect or destroy the infectious potential of medical waste and to transform it into material which would not adversely impact the overall environment.

BRIEF SUMMARY AND OBJECTS OF THE INVENTION

The present invention provides an apparatus and method of processing medical waste, including medical and veterinary waste, which disinfects and transforms medical waste by disintegrating or shredding the waste, exposing the waste to radio-frequency (RF) heating, and transforming the disinfected materials into such useful material as reclaimed plastic or refuse-derived fuel.

One step in the method comprises shredding or disintegrating the medical waste into fragments, compacting the fragments and placing the fragments in closed, heat-resistant containers. Another step in the method includes heating the repackaged medical waste fragments with RF waves to raise the internal temperature of the package to about 90–100° C., after which the waste is optionally held at that temperature for at least two hours.

The invention additionally includes steps for further transformation of pre-sorted medical and veterinary waste into either recycled plastic or refuse-derived fuel.

Therefore, in view of the foregoing, primary objects of the present invention are to disinfect medical waste into useful materials by heating the waste and to transform the waste in an environmentally safe manner.

Additional objects, advantages and novel features of the invention will be set forth in part in the description which follows, and in part will become apparent to those skilled in the art upon examination of the following or may be learned by practice of the invention.

The objects and advantages of the invention may be obtained by means of the methods and combinations particularly pointed out in the appended claims.

DETAILED DESCRIPTION OF THE PREFERRED EMBODIMENTS

The present invention relates to an apparatus and a method for processing medical waste. Medical and veterinary wastes are disinfected, or rendered incapable of causing an infection. The present method inactivates microorganisms in medical and veterinary waste so that the waste can no longer cause an infection. Such disinfection is accomplished by the application of RF radiation. Then additional parts of the apparatus and method relate to converting the disinfected waste into useful material, either reclaimed plastic or compact, relatively low-sulfur fuel.

Disintegrating or Shredding the Waste

Figure 1:
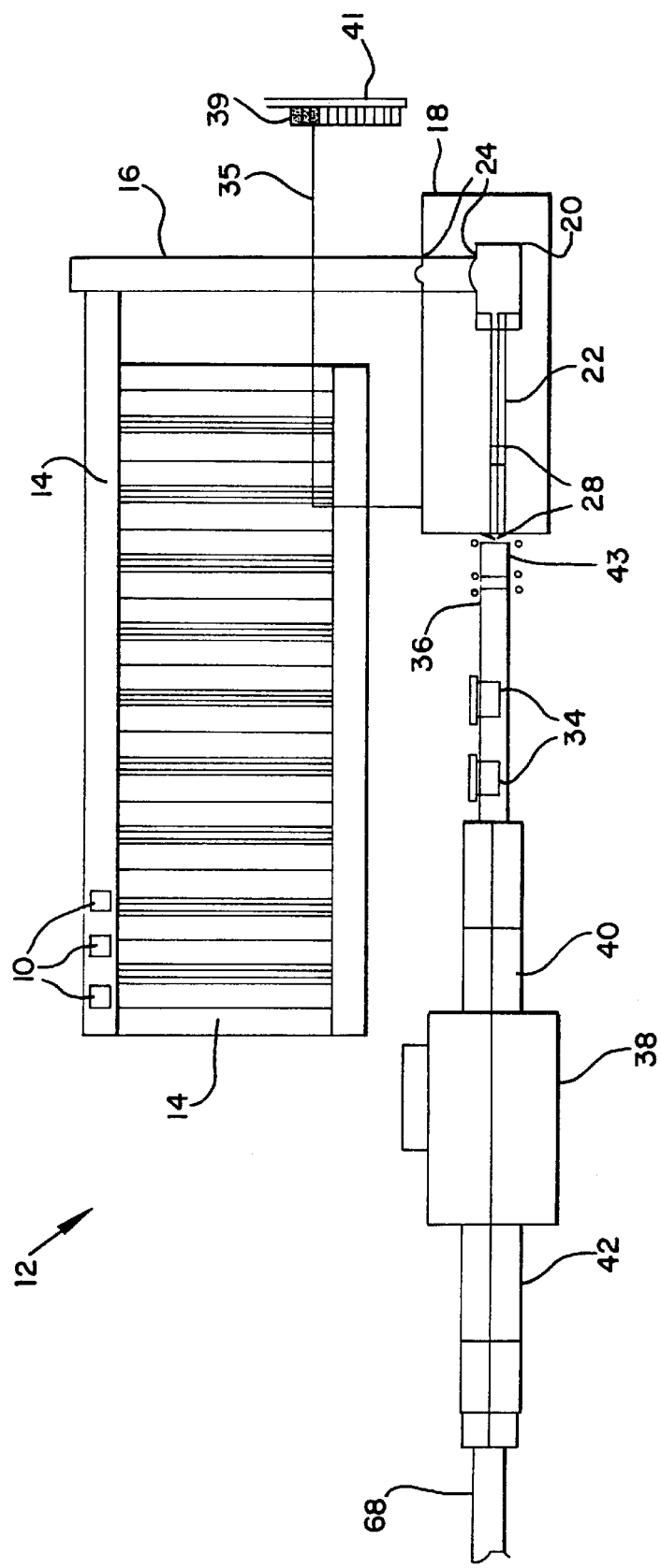
FIG. 1 shows a plan view diagram of the apparatus for handling and processing of medical and veterinary waste according to the invention.

As input to the apparatus of the present invention, as shown in FIG. 1, medical waste in sealed boxes 10 arrives at the medical waste processing facility 12 and is unloaded onto a conveyor belt 14 where all boxes 10 in each load are segregated and counted. The shredder load conveyor 16 carries the boxes 10 into the pre-processing room 18. The pre-processing room 18 contains the shredder 20 and screw conveyor 22 which are designed to disintegrate medical waste into fragments and move the fragments to other containers 34 for disinfection. As herein defined, disintegration refers to breaking up or shredding materials to a relatively uniform size that is no larger than about 1½ inches.

Figure 2:
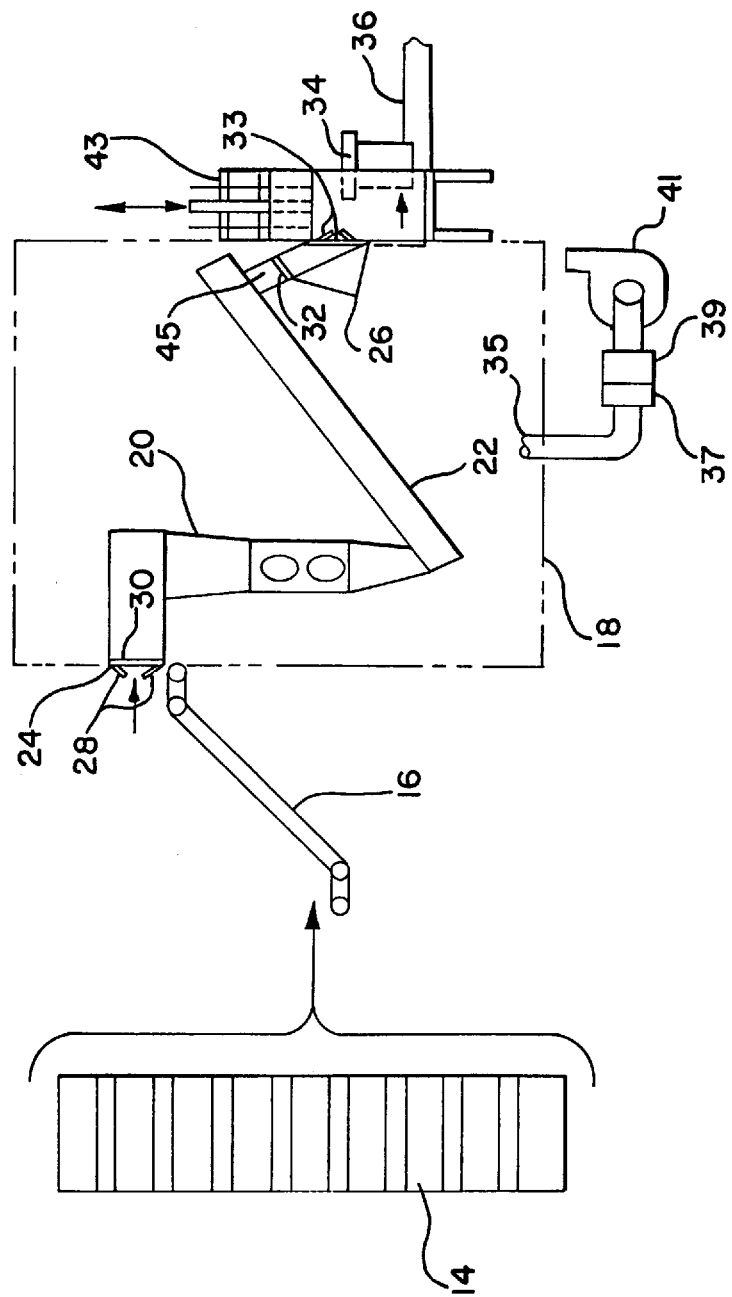
FIG. 2 is a schematic showing primarily the pre-processing apparatus of the invention.

As shown in FIG. 2, the pre-processing room 18 has several features to prevent the escape of contamination from the room 18. First, entry and exit of medical waste in the pre-processing room 18 is controlled by two sets of airlocks, inlet airlocks 24 and outlet airlocks 26. Each set of airlocks consists of two sets of doors, 28, 30 and 32, 33, respectively. To enter the preprocessing room 18, the boxes 10 of medical waste pass through the first set of doors 28, which closes behind the boxes 10. After the first set of doors 28 closes, the second set of doors 30 opens and permits the boxes 10 to enter the pre-processing room 18. The exit doors 32, 33 operate similarly to the inlet doors 28, 30. Thus, there is always at least one set of exit and entry doors closed at any time.

In addition to the airlocks 24 and 26, airflow is further controlled by heated and filtered room exhaust ducts 35. Electric duct heaters 37 keep the temperature in the ducts 35 at about 82° C. which is sufficient to destroy any viruses. Across the ducts 35 are high-efficiency particulate air (HEPA) filters 39 having pores of 3 microns and an efficiency of 99.7% in preventing bacteria from escaping. These room exhaust ducts 35 control the airflow into and out of the sealed pre-processing room 18. One large fan 41 pulls air out of these ducts 35 at the rate of about 1,000 cubic feet per minute. This fan produces "negative" air pressure which helps prevent possibly contaminated air from the pre-processing room 18 from flowing back into the rest of the facility 12. The heated, filtered air is vented to the outside environment.

In addition to the room exhaust duct 35, there are heated, filtered ducts (not shown) connected to the shredder 20, the screw conveyor 22 and the pneumatic press 43 which vent to the outside environment in the same fashion as described for the room exhaust ducts 35.

As shown in FIG. 2, the boxes 10 of medical waste enter the pre-processing room 18 on conveyor 16 and are emptied into shredder 20. The disintegration or shredding is performed by two sets of cutting blades (not shown) rotating at 1800 revolutions per minute which are powered by 50-horsepower motors (not shown). The shredder 20 turns the medical waste into fragments which measure about 1.5 inches in their greatest dimension. Shredding also reduces the volume of the medical waste by about one half. A suitable shredder is Model No. 005371-D available from Shredding Systems, Inc., Wilsonville, Oreg., which measures about 12 feet tall, 10 feet wide and 12 feet long.

The waste fragments exit the shredder 20 via a screw conveyor 22 which operates inside a tube and which further carries the medical waste fragments vertically to the conveyor tube 45 from which the fragments drop into the pneumatic press 43. The pneumatic press 43 compresses the medical waste fragments into heat-resistant plastic polyethylene containers 34 which measure 24 inches by 24 inches by 18 inches and weigh about 50 pounds. As defined herein, heat-resistant means that the containers do not soften or melt during the heating process and that the containers keep the temperature of medical waste within about 8° C. when stored at room temperature (25° C.) for one hour. The containers 34 include snug but not air-tight lids. A suitable container is Model No. 24, available from Chem-Tainer, Babylon, N.Y. Each container 34 is filled with about 200 pounds of compacted waste fragments. At this time, water may be added, but is not usually necessary. Alternately, a foam is sprayed on medical waste fragments having a high metallic content. Water and foam are thought to help disperse the heat and avoid fires. Then the cover is attached snugly to the filled container 34.

The pneumatic press 43 further compacts the medical waste fragments to less than one half the volume the container 34 receives. Hence, the total reduction in medical waste volume from receipt at the facility 12 to closing of the container 34 is about five to one. In this manner, wastes which enter the pre-processing room 18 with a density of five (5) pounds per cubic foot exit the room 18 at densities of 25 pounds per cubic foot. It can be seen that dissimilar wastes, namely paper, plastics, glass, metal and fluids are converted into the more uniform sizes and densities required for a mechanized RF heating chamber.

Disinfection

Next, as shown in FIG. 1, the sealed containers 34 of medical waste fragments are transported away from the pre-processing room 18 and into the dielectric heater 38 for volumetric heating by RF waves. RF waves are a form of electromagnetic energy. They also transfer energy directly into materials, primarily by the interaction of their time-varying electric fields with molecules. RF waves may be applied by connecting a RF alternating current to a pair of electrodes. Between the two electrodes an alternating RF electro-magnetic field having a time-varying electric field component is established. When objects are placed between the electrodes in the time-varying electric field, the time-varying electric field partially or completely penetrates the object and heats it.

Heat is produced when the time-varying electric field accelerates ions and electrons which collide with molecules. Heat also is produced because the time-varying electric field causes molecules, and particularly those with a relatively high electric dipole moment, to rotate back and forth as a result of the torque placed upon them by the time-varying electric field. Most large molecules, or molecules with evenly distributed charges, have relatively low or nonexistent dipole moments and are not very much affected by the RF time-varying electric field. Small molecules, in particular polar groups, have relatively large electric dipole moments and thus have relatively large torques exerted upon them by the time-varying electric field. In particular, highly polar molecules, like water, experience relatively large torques and as a result are rotated by the time-varying electric field. The mechanical energy of rotation is transferred to surrounding materials as internal energy or heat. Lower frequency time-varying electric fields penetrate deeply and heat objects more evenly. Relatively high frequency time-varying electric fields do not penetrate as deeply, but heat more rapidly the portions of objects they interact.

Because different materials are composed of different types of molecules with differing electric dipoles, they heat at different rates when exposed to a given RF field. For example, plastics, which are composed of very large molecules (polymers), are not heated by RF fields as rapidly as water. Metal objects may or may not be easily heated when exposed to RF fields, because their high conductivity tends to short out the electric fields and rescatter them. As a consequence, there are many conditions under which metal objects are difficult to heat. On the other hand, such RF fields can also induce substantial currents which flow on the outside of the metal objects.. Under certain circumstances, heating effects will occur on the surface of the metal object which, in the case of a small needle, the heat is readily diffused into the interior. In addition, the presence of long, thin metal objects in an electric field causes enhancement of the electric field intensity near the ends of these metal objects and a diminution or shadowing of the fields near the middle. Thus, if the electric field is parallel to the axis of the metal object, strong electric fields will exist near the tips and weak electric fields will exist near the center of the rod or needle. Such field enhancements can lead to arcing and possible fires.

As mentioned above, the containers 34 of compacted medical waste fragments enter the dielectric heater 38, and do so through an entry tunnel 40. The dielectric heater 38 generates RF waves, which heat the waste as described above. The waste fragment containers 34 are uniformly or volumetrically heated in the electric field for about five minutes. As a result of this exposure to RF waves, the waste reaches temperatures of about 90°–100° C.

The covered containers 34 move along a conveyor 36 into the dielectric heater 38 which measures 38 feet long, 13 feet wide and 10 feet high. The dielectric heater 38 weighs 28,000 pounds. Two eight-foot tunnels 40 and 42, form the entry and exit portions respectively, of the dielectric heater 38. The tunnels attenuate RF waves and prevent RF leakage from the dielectric heater 38. In the 20-foot-long RF chamber or oven 44, a system of exciter and ground electrodes 46 generate electromagnetic waves in the RF band. The RF band is between audio and infrared frequencies and includes approximately 10 kilohertz (KHz) to 300 gigahertz (GHz). When the electrode system 46 is supplied with radio frequency power, it projects an electromagnetic wave into the target containers 34 of medical waste.

The RF waves effectively penetrate the containers 34 of medical waste. The medical waste absorbs these waves whose energy is thought to produce heat by inducing dipole rotation and molecular vibration. When RF waves are absorbed, they may cause differential heating. Moist articles and metal objects in the containers 34 absorb more waves and may create "hot spots," or uneven heating; but prior disintegration and compaction of the medical waste fragments avoids serious arcing and speeds heat transfer. In the covered containers 34, steam and heat from the hotter fragments are rapidly redistributed to the entire contents of the containers 34. Since the containers 34 are not air tight, steam gradually escapes and there is no excessive pressure buildup.

Figure 3:
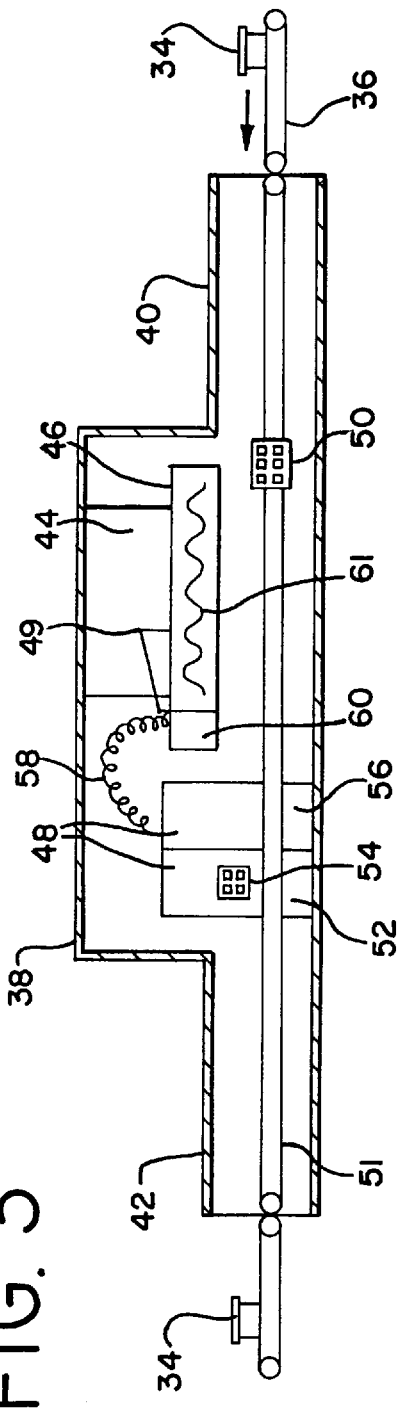
FIG. 3 is a schematic of the radio-frequency heater of the invention.

As shown in FIG. 3, the dielectric heater 38 has the following components: a generator 48, an applicator 49 and controls 50. In addition, conveyor 51 moves the medical waste containers 34 through the dielectric heater 38.

The generator 48 has a power supply 52, voltage controls 54 and a radiator source 56. The generator 48 measures 14.5 feet long, 3.5 feet wide and 7 feet high. It is fabricated of 10-gauge steel and aluminum with a four-inch channel base and a 0.25-inch thick steel base plate. The generator 48 has two dust-tight compartments with doors. These compartments contain the power supply 52 and radiator source 56. The power supply 52 and voltage controls 54 provide high-voltage direct current to the radiator source 56. Preferably, the generator 48 generates about 50 to about 150 kilowatts of power. More preferably, about 100 to about 150 kilowatts of power are generated. The power supply 52 compartment includes a 300 kilowatt, three-phase power transformer (not shown), which converts 60-cycle alternating current to direct current, as well as six stack silicon diode rectifiers and other equipment (not shown).

The radiator source 56 generates high-frequency power. Preferably, the frequency is in the range of about 5 to about 100 megahertz. More preferably, the frequency is in the range of about 5 to about 25 megahertz. Most preferably, the frequency is about 13 megahertz. An oscillator (not shown) is preferred to generate the high-frequency power, although an amplifier (not shown) also may be used. A suitable oscillator is Model No. 3CW150000 from Eimac (Division of Varian, 301 Industrial Way, San Carlos, Calif.). An alternate for this purpose is Siemens Model No. RS3300CJ oscillator which is available from Siemens Components, 186 Wood Avenue, Islin, N.J. The radiator source also has a water supply (not shown) of approximately 25 gal/min at about 20° C. for cooling. A coaxial cable 58 feeds high-frequency power from the radiator source 56 into the heater applicator 49.

The heater applicator 49 consists of a matching network 60 and system of electrodes 46 and is located in the oven 44 which is a portion of the dielectric heater 38. The oven 44 which is 20 feet long, 13 feet wide and 10 feet high is constructed of 0.25-inch aluminum plate and 10-gauge aluminum sheet. The main body of the electrode system 46 is a 7-foot by 14-foot aluminum electrode whose height is adjustable from 28–40 inches by means of a reversible gear motor (not shown). The motor is operated by a three-position selector switch on an external control panel 50, which also displays electrode height. Heater elements 61 are mounted on the electrode 46 with a suitable RF pi-filter network (not shown) for decoupling the electrode heaters 61 from the rest of the RF circuit. The matching network 60 has a meter relay and amplifier (not shown) which, in combination with a motor-driven variable capacitor (not shown) automatically maintains power output at a preset level that is even throughout the oven 44. The coaxial cable 58 from the radiator source 56 connects to the matching network 60 which in turn feeds power into the electrode 46 to convert RF electricity into a RF magnetic field. Containers 34 of medical waste fragments which pass through the field are heated as described above.

The containers 34 leave the dielectric heater 38 via the exit tunnel 42. After exiting the tunnel 42, the containers 34 of disinfected medical waste go to other stations for processing as described in detail below. Alternately, the containers 34 may be held in a room (not shown) with a 90°–95° C. temperature before further processing as described below. Preferably, the containers 34 are held in the room for a time sufficient to further disinfect medical waste. Preferably, the time in the heated room would be about one to six hours. More preferably, the containers 34 would remain in the heated room about one hour.

Processing Into Useful Materials

Figure 4:
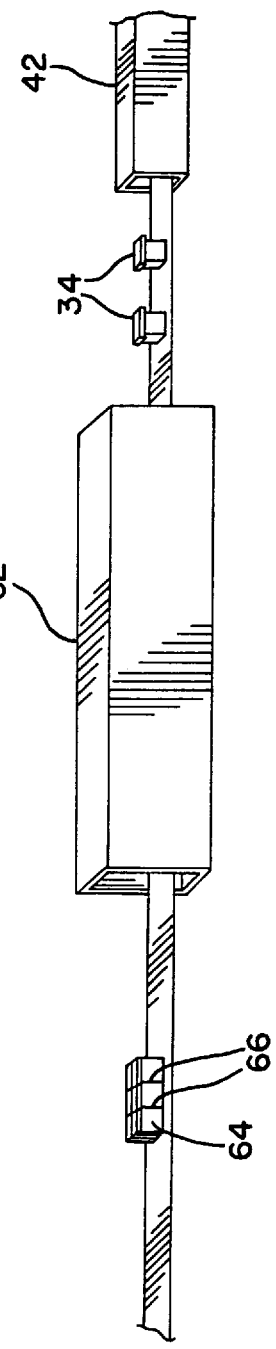
FIG. 4 is a schematic showing of the refuse-derived fuel apparatus of the invention.

The disinfected waste is next turned into useful materials such as refuse-derived fuel, or separated into useful components such as plastic or metal. As shown in FIG. 4, the disinfected waste, after leaving the exit tunnel 42, is emptied from the heating containers 34 into a large compressing means, or baler 62, to compress the wastes into a dense cube 64 which can be secured by baling wires 66. These dense cubes 64 of processed medical waste, or refuse-derived fuel, leave the facility 12 and are transported to high-temperature burning devices such as cement kilns (not shown). The baler 62 of the present invention is 180 inches long, 50 inches wide and 76 inches high. It is powered by a 15-horsepower electric motor (not shown) which can generate a "press weight" of 7,000 pounds. The baler 62 is filled with disinfected waste fragments compressed to a dense cube 64 measuring three feet by six feet by 2.5 feet. Each cube 64 is secured by four thin baling wires 66. Each baled cube weighs approximately 1200 pounds. A forklift (not shown) loads baled cubes onto trucks for transport to regional cement kilns.

Laboratory analyses (Tables A, B, C and D) have shown that this processed medical waste has a BTU value of at least 12,016 per pound (Table A),,comparing very favorably with the BTU value of coal, which ranges from about 11,000 to about 15,000 per pound. The sulfur content of the processed medical waste is less than 0.2% (Table A), and is lower than that of coal, which can vary from about 0.3% to about 4.0%. At the temperature at which cement kilns operate, (2800° C.), the plastics in the medical waste burn completely to carbon dioxide and water and form no harmful intermediate breakdown products, such as furans and dioxins (Table D).

TABLE A

RESULTS FROM BURNING PROCESSED MEDICAL WASTE
(Gabriel Laboratories, Inc.)

|  | As Received | Dry Basis |
|---|---|---|
| Moisture (%) | 3.18 | — |
| Ash (%) | 2.78 | 2.87 |
| Volatiles (%) | 86.58 | 89.42 |
| Fixed Carbons (%) | 7.46 | 7.71 |
| TOTAL | 100.00 | 100.00 |
| Heat Production (BTU/lb) | 11,346 | 12,016 |
| Sulfur (%) | 0.11 | 0.11 |

TABLE B

MINERAL ANALYSIS OF PROCESSED MEDICAL WASTE ASH
(Gabriel Laboratories, Inc.)

| Mineral | Weight, Dry Basis (%) |
|---|---|
| Silica (SiO) | 24.61 |
| Alumina ($Al_2O_3$) | 12.49 |
| Titania ($TiO_2$) | 34.00 |
| Ferric Oxide ($Fe_2O_3$) | 7.69 |
| Lime (CaO) | 4.96 |
| Magnesia (MgO) | 1.23 |
| Potassium Oxide ($K_2O$) | 1.31 |
| Sodium Oxide ($Na_2O$) | 6.91 |
| Sulfur Trioxide ($SO_2$) | 7.81 |
| Phosphorus Pentoxide ($P_2O_5$) | 1.20 |
| Manganese Dioxide ($MnO_2$) | 0.08 |

TABLE C

LABORATORY ANALYSIS OF PROCESSED MEDICAL WASTE
(National Environmental Testing, Inc.)

| Ash (%) | 4.2 |
|---|---|
| Heat Production (BTU/lb) | 15,900 |
| Chlorine, Total (%) | <0.1 |
| Solids, Total (%) | 98.88 |
| Sulfur, Total (%) | 0.20 |
| Arsenic ($\mu$g/g ash) | <0.25 |
| Cadmium ($\mu$g/g ash) | <0.15 |
| Chromium, Total ($\mu$g/g ash) | 2.6 |
| Lead ($\mu$g/g ash) | 3.6 |
| Mercury ($\mu$g/g ash) | 1.0 |
| Nickel ($\mu$g/g ash) | 1.7 |
| Physical Characteristics | solid |
| Color | multicolored |
| Corrosivity (pH units) | 6.82 |

TABLE D

VOLATILE COMPOUNDS FROM INCINERATED
BALED MEDICAL WASTE
(National Environmental Testing, Inc.)

| Compound | Content (ng/g) |
|---|---|
| Acrolein | <1000 |
| Acryonitrile | <1000 |
| Benzene | <100 |
| Bromodichloromethane | <100 |
| Bromoform | <100 |
| Bromomethane | <1000 |
| Carbon Tetrachloride | <100 |
| Chlorobenzene | <100 |
| Chloroethane | <1000 |
| 2-Chloroethylvinyl ether | <100 |
| Chloroform | <100 |
| Chloromethane | <1000 |
| Dibromochloromethane | <100 |
| 1,2-Dichlorobenzene | <100 |
| 1,3-Dichlorobenzene | <100 |
| 1,4-Dichlorobenzene | <100 |
| 1,1-Dichloroethane | <100 |
| 1,2-Dichloroethane | <100 |
| cis-1,2-Dichloroethane | <100 |
| trans-1,2-Dichloroethane | <100 |
| 1,2-Dichloropropane | <100 |
| cis-1,3-Dichloropropane | <100 |
| trans-1,3-Dichloropropane | <100 |
| Ethyl benzene | <100 |
| Methylene chloride | <100 |
| 1,1,2,2-Tetrachloroethane | <100 |
| Tetrachloroethane | <100 |
| Toluene | <100 |
| 1,1,1-Trichloroethane | <100 |
| 1,1,2-Trichloroethane | <100 |
| Trichloroethane | <100 |
| Trichlorofluoromethane | <100 |
| Vinyl chloride | <1000 |
| Xylenes, Total | <100 |
| PCB's | ($\mu$g/g) |
| PCB-1016 | <0.10 |
| PCB-1221 | <0.10 |
| PCB-1232 | <0.10 |
| PCB-1242 | <0.10 |
| PCB-1248 | <0.10 |
| PCB-1254 | <0.10 |
| PCB-1260 | <0.10 |

Plastics Reclamation

Another way disinfected medical waste fragments can be transformed into useful material is through plastics reclamation. Plastics reclamation is also performed after disinfection of medical waste fragments in the dielectric heater 38. Long before their arrival at the processing facility 12, many of the medical plastics, or sharps, are routinely segregated immediately after use by healthcare workers. Syringes, manufactured from natural polypropylene, are typically discarded immediately after use in special plastic containers designed for this purpose. These plastic containers are usually manufactured from natural polypropylene. These sharps and their containers are then placed in separate sharps waste boxes. When these sharps waste boxes arrive at the processing facility 12, the sharps boxes are segregated and handled separately from other medical waste. Sharps go through the same pre-processing and disinfection steps described above. Preferably, sharps fragments are sprayed with water or a foam consisting of detergent and water, to help disperse heat from the metal fragments. Any household detergent may be used for this purpose.

After disinfection, segregated sharps fragments do not go directly to the baler 62. The sharps undergo a series of separation steps, in which desired materials undergo further separation and other separated materials are routed to the baler 62.

Figure 5:
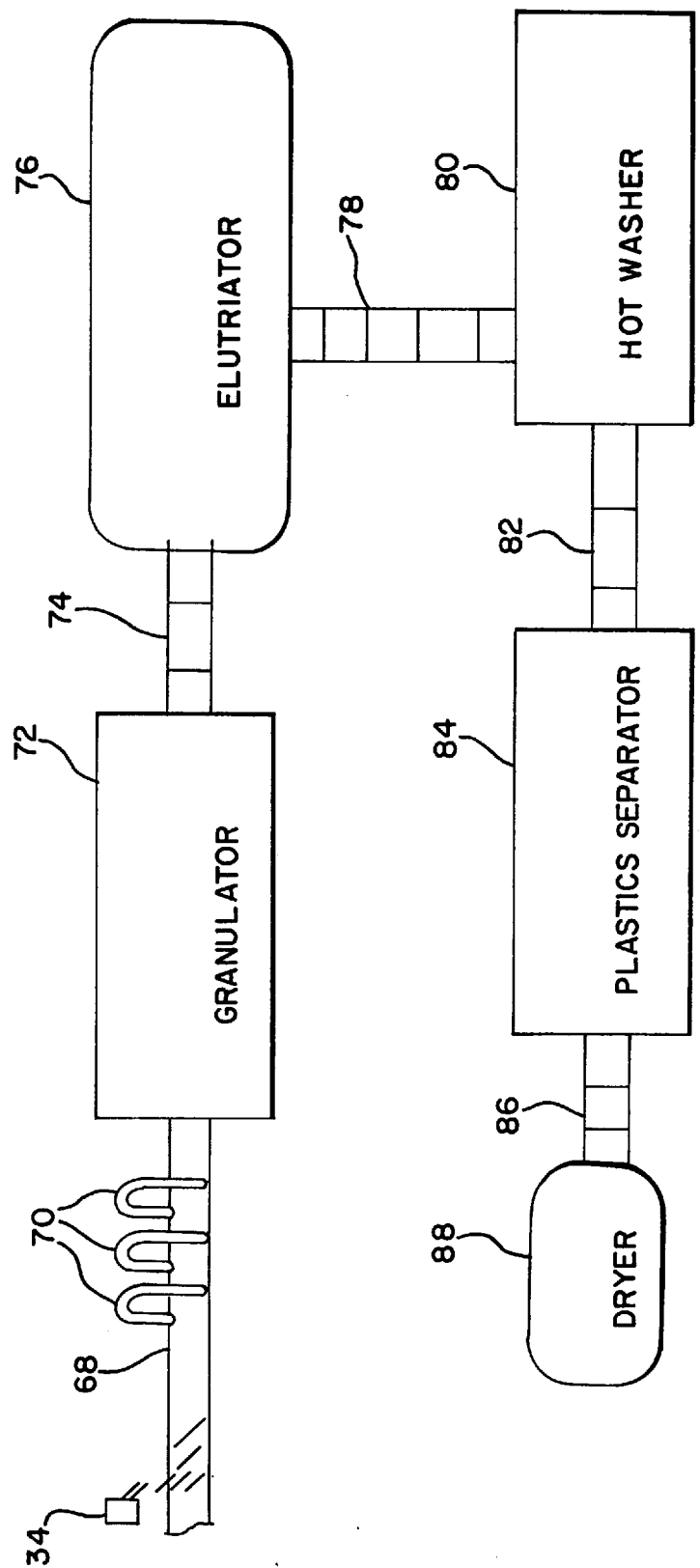
FIG. 5 is a schematic showing the plastics reclamation apparatus of the invention.

Preferably, the sharps have undergone the preprocessing and disinfection described above. Next, as shown in FIG. 5, the cover is removed from the medical fragment container 34, and the disinfected fragments are deposited on conveyor belt 68. The belt 68 carries the fragments through a series of magnets 70 which remove ferrous and non-ferrous metals, such as needles and wire catheters, from the waste stream. The non-metallic fragments remain on the belt 68. At the end of belt 68 is plastics granulator 72. The plastics granulator 72 turns fragments of non-metallic sharps into fine particles having no dimension larger than about one eighth inch. As the particles exit the plastics granulator 72 on a conveyor belt 74, they pass in front of a hot air blower (not shown) which dries the particles.

The conveyor belt 74 carries the particles to a device called an elutriator 76, which separates and removes particles by their density. In the elutriator 76, the particles are exposed to a blast of air. Lighter, less dense particles such as paper pieces are carried to the top of the elutriator 76, and heavier, denser particles such as rubber and glass pieces fall to the bottom of the elutriator 76. The plastic particles segregate in one definable layer which is carried via the conveyor 78 to the hot washer 80. Other, non-plastic particles are collected and placed in the baler 62 to be compacted into dense cubes 64.

In the hot washer 80, ink and paper are washed off the plastic particles. In addition, cardboard, thick papers and other materials not removed in the elutriator become soaked with water and sink to the bottom of the hot washer 80. This material is removed as waste from the bottom of the hot washer 80. The waste from the hot washer 80 also is removed to the baler 62. Washed plastic particles are transported via conveyor 82 to plastics separator 84.

Next, the plastic particles enter the plastics separator 84, which is another type of elutriator to classify different types of plastic (and other materials) by their buoyancy in liquid. The plastics separator 84 is highly effective in selecting for polypropylene. Non-polypropylene materials are removed in the process and are sent to the baler 62. The polypropylene coming from the plastics separator 84 is as much as 99.999% pure polypropylene.

Finally, the conveyor 86 carries the polypropylene particles to a dryer 88 which removes all moisture present on the particles. The dried polypropylene is then ready to be flaked (not shown) and thence made into such items as waste baskets, recycling bins and sharps disposal containers.

A suitable plastics granulator, elutriator, hot washer, plastics buoyancy separator and drier can all be obtained from Sepco, Spokane, Washington.

Another embodiment of the invention stops the reclamation process after the hot washing step performed by the hot washer 80. At that point, the plastics are relatively devoid of non-plastic elements and can be dried and flaked for resale.

The foregoing descriptions of the preferred embodiments of the present invention have been presented for purposes of illustration and description. They are not intended to be exhaustive or to limit the invention to the precise forms disclosed, and obviously many other modifications and variations are possible in light of the above teachings. The embodiments were chosen and described to best explain the principles of the invention and its practical applications, thereby enabling others skilled in the art to best utilize the invention in its various embodiments and with various modifications as are suited to the particular use contemplated. It is intended that the scope of the invention be defined by the following claims, including all equivalents.

EXAMPLES

Example 1

Mixed medical waste was shredded and compacted according to the present invention and placed in 100 plastic containers made of polyethylene plastic, measuring 24 inches by 24 inches by 18 inches and weighing 50 pounds before filling. Each container was divided into four quadrants, into which temperature sensitive probes were placed. The temperature-sensitive tip of each probe was inserted to a depth of about two inches, which was considered the "coldest" spot in the waste container and least likely to reach the required temperature during passage through the dielectric heater. Then the covers were secured to the top of the containers. Each container was exposed to RF radiation in the frequency of 13 megahertz and an electric field strength of 50,000 volts per meter for approximately five minutes. The temperatures were recorded and tabulated as shown below:

| Mean Temperature | 94° C. |
|---|---|
| Standard Deviation | 3.0° C. |
| Minimum Temperature | 91° C. |
| Maximum Temperature | 102° C. |
| Range | 11° C. |

TEMPERATURE FREQUENCY DISTRIBUTION (°C.)

| Range (°C.) | Count | Percent |
|---|---|---|
| From 85 up to 90 | 0 | 0 |
| From 90 up to 95 | 51 | 51 |
| From 95 up to 100 | 47 | 47 |
| From 100 up to 105 | 2 | 2 |

These statistics illustrate the evenness of the heating, in spite of the diverse nature of medical waste.

Example 2

Approximately 60 plastic containers were filled with about 200 pounds of medical waste that had been shredded and compacted according to the present invention. The plastic containers were made of polyethylene plastic, measuring 24 inches by 24 inches by 18 inches and weighing 50 pounds before filling. Into each container at a depth of about two inches were placed test tubes containing viruses and controls. Temperature-sensitive indicators were attached to the top and bottom of each test tube. Then a cover was secured to each container. The viruses used for the study were Herpes simplex virus (HSV), type 2 (ATCC VR-540) and Poliovirus 3 (ATCC VR-193). To ensure a homogeneous and adequate supply of viruses for the study, stocks of HSV and poliovirus were grown prior to the initiation of the testing, harvested, frozen and validated according to standard methods.

The medical waste containers were divided into eight treatment groups as shown below:

| Group | Time in Dielectric Heater (min) | Standing Time (min) |
|---|---|---|
| 1 | 4 | 0 |
| 2 | 4 | 20 |
| 3 | 10 | 0 |
| 4 | 10 | 20 |
| 5 | 6 | 0 |
| 6 | 6 | 20 |
| 7 | 8 | 0 |
| 8 | 8 | 20 |

Control test tubes of viruses were held at room temperature (about 25° C.) while the containers of medical waste with test viruses were subjected to sufficient RF radiation to bring the temperatures of the containers to approximately 60° C. Immediately after the standing period (additional time spent at room temperature), the containers were opened and the virus tubes removed and all tubes were sent to the microbiological laboratory. The temperature strips were removed and temperatures recorded. In all instances except three, the temperature exceeded 60° C.; and at least one of those failures appeared to be due to a malfunctioning temperature strip.

To determine the success of the disinfection, the viruses in the test tubes were first diluted multiple times. An aliquot from each of the dilutions was tested for its ability to still kill cells, according to standard methods. Only HSV and poliovirus from control tubes (which were not subject to dielectric heating) showed continued ability to kill cells, even when diluted by a factor of $10^5$. None of the HSV or poliovirus from heated tubes (Groups 1–8) showed any ability to kill cells, even when diluted only by a factor of 10.

Thus, the virus validation study demonstrated that the process completely and uniformly destroys viruses even when the wastes are only heated to about 60°–70° C. and maintained at those temperatures for only about 10–30 minutes. Because the dielectric heater of the present invention heats medical waste to 90°–98° C., there is a large margin of safety for viral kill.

Example 3

Five medical waste containers each filled with about 200 pounds of medical waste fragments according to the method of the present invention were selected and the covers were removed. Five strips of *Bacillus subtilis,* var. *niger* spores were deposited in each container. The spore strips were placed on top of the waste fragments, at the air-waste interface. This is the region of the waste container least likely to retain heat, because the heated waste gives up heat to the cooler air at this interface. Each spore strip contained about one million spores ($10^6$). *B. subtilis* spores were chosen because they are highly resistant to heat treatment.

The covers were replaced on the medical waste containers and four of the five containers were run through the dielectric heater according to the method of the present invention. The fifth waste container did not pass through the dielectric heater and served as the control for the experiment. Each of the four containers passed through the 50,000 volt/m electric field. The dwell time, or time the containers spent in the electric field, was five minutes. The frequency of the radiowaves was 13 megahertz.

As soon as the containers left the dielectric heater, temperature probes were placed into the four quadrants of each waste container to record the initial temperatures, which were averaged. After standing for one hour at room temperature (about 25° C.), the first container was opened, the internal temperature was recorded and the spore strips were withdrawn. After standing for two hours at room temperature, the second container was opened, the internal temperature was recorded and the spore strips were withdrawn. The third and fourth containers were opened at three and four hours, respectively, and handled the same.

According to standard method, the spores were diluted and cultured with the following results:

| Standing Time (hours) | Temperature Initial (°C.) | Temperature Final (°C.) | Spore Concentration | Log Reduction |
|---|---|---|---|---|
| 1 | 98 | 92 | $8.5 \times 10^2$ | 4 |
| 2 | 97 | 92 | $6.0 \times 10$ | 5 |
| 3 | 100 | 84 | $9.0 \times 10$ | 5 |
| 4 | 95 | 81 | $7.5 \times 10$ | 5 |
| Control | NA | NA | $1 \times 10^6$ | 0 |

This test proves that exposing the waste containers to RF radiation for five minutes is sufficient to produce a four log reduction with only one hour of standing time and five log reductions with longer standing times. In addition, as long as the containers stayed closed, the heavy, 50-pound containers lost only about 4–8° C. per hour when the containers were in a 25° C. room. Because vegetative (non-spore) bacteria, yeasts and fungi are all less resistant to heat than are *B. subtilis* spores, these organisms would all be effectively eliminated by treatment according to the present invention.

We claim:

1. An apparatus for processing medical waste that comprises plastic material and a metallic material comprising:
   a conveyor to receive and move medical waste that comprises plastic material and a metallic material to a shredder;
   a shredder to receive said medical waste from said conveyor and to break up said medical waste into fragments no larger than about one and one half inches;
   a second conveyor to receive said medical waste fragments from the shredder and to move said medical waste fragments to a portable container;
   a portable container to receive and contain said medical waste fragments from said second conveyor;
   a press to compact said medical waste fragments contained in said portable container to produce compacted medical waste fragments;
   a third conveyor to convey said portable container with compacted medical waste fragments into a dielectric heater;
   a dielectric heater to disinfect said compacted medical waste fragments contained in said portable container by generating an electromagnetic field that is transmitted through said portable container and interacts with said compacted medical waste fragments so as to raise the temperature of said compacted medical waste fragments to about 90°–100° C. within about 5 minutes, wherein said dielectric heater has a structure so as to control the generated electromagnetic field so that said compacted medical waste fragments reach a temperature level that produces disinfected and compacted medical waste fragments and allow substantially all of said plastic material to be reclaimed; and
   a baler to accept said disinfected and compacted medical waste fragments from the portable container and to compress said disinfected and compacted medical waste fragments into a single piece.

2. The apparatus of claim 1, which further comprises upstream from the baler:
   a magnet to remove metallic fragments from said disinfected and compacted medical waste fragments, leaving non-metallic fragments;
   a plastic granulator located downstream from the magnet, said plastic granulator reducing the size of said non-metallic fragments to non-metallic particles no larger than about one-eighth inch;

an elutriator located downstream from the plastic granulator, said elutriator separating plastic particles from other non-metallic particles by exposing the non-metallic particles to a blast of air;

a hot washer located downstream from the elutriator, said hot washer removing paper, ink labels, and other objects from the plastic particles; and a plastic separator located downstream from the hot washer, said plastic separator separating polypropylene particles from other plastic particles.

3. The apparatus of claim 2 further comprising a dryer located downstream from the plastic separator, said dryer removing moisture from the polypropylene particles.

4. The apparatus of claim 1, wherein said temperature is raised to about 90° C. to 100° C.

* * * * *

UNITED STATES PATENT AND TRADEMARK OFFICE
CERTIFICATE OF CORRECTION

PATENT NO. : 5,830,419
DATED : November 3, 1998
INVENTOR(S) : Jeffery S. Held et al.

It is certified that error appears in the above-indentified patent and that said Letters Patent is hereby corrected as shown below:

On the Title Page

In column 1, line 8, under "Related U.S. Application Data", please change "Oct. 3" to --Oct. 13--.

In column 2, line 10, under "OTHER PUBLICATIONS", please change "Unkonwn" to --Unknown--.

In the Claims

Please cancel claim 36.

Signed and Sealed this

Seventeenth Day of April, 2001

Attest:

NICHOLAS P. GODICI

Attesting Officer   Acting Director of the United States Patent and Trademark Office